United States Patent [19]

Loveless et al.

[11] 3,932,308

[45] Jan. 13, 1976

[54] HYDROGENATION CATALYST

[75] Inventors: Fredrick C. Loveless, Oakland, N.J.; Don H. Miller, Warren, Mich.

[73] Assignee: Uniroyal Inc., New York, N.Y.

[22] Filed: Oct. 9, 1974

[21] Appl. No.: 513,373

Related U.S. Application Data

[62] Division of Ser. No. 224,977, Feb. 9, 1972, Pat. No. 3,855,185.

[52] U.S. Cl. .......................... 252/431 R; 252/431 C
[51] Int. Cl.$^2$ ............................................ C07C 5/02
[58] Field of Search ...................... 252/431 R, 431 C

[56] References Cited
UNITED STATES PATENTS

| | | | |
|---|---|---|---|
| 3,412,174 | 11/1968 | Kroll | 252/431 R |
| 3,531,450 | 9/1970 | Yoshimoto et al. | 252/431 R |
| 3,855,185 | 12/1974 | Loveless et al. | 252/431 R |

*Primary Examiner*—Helen M. McCarthy
*Attorney, Agent, or Firm*—James J. Long

[57] ABSTRACT

A hydrogenation catalyst is prepared by:

A. providing a hydrocarbon-soluble catalyst precursor which is a reaction product of (a) a transition metal compound (e.g. nickel acetylacetonate) with (b) a phenolic substance (e.g. p-nonylphenol); and B. reducing the soluble precursor with (c) an organometallic reducing agent (e.g. n-butyllithium) in a solvent medium to form a highly active catalyst.

The catalyst is useful for hydrogenating polyisoprene, EPDM, 1-octene, etc.

15 Claims, No Drawings

HYDROGENATION CATALYST

This is a division of application Ser. No. 224,977, filed Feb. 9, 1972, now U.S. Pat. No. 3,855,185.

This invention relates to a hydrogenation catalyst, a method of making same, and a hydrogenation process employing such catalyst.

In one aspect, the invention involves the preparation of a highly active hydrogenation catalyst from a soluble precursor, by subjecting the precursor to the action of an organometallic reducing agent. More particularly, the invention contemplates first providing, as a catalyst precursor, a hydrocarbon-soluble organometallic complex which is a reaction product of (a) an organic chelate compound of a transition metal with (b) a phenolic substance. The thus-formed organometallic complex, or soluble catalyst precursor, is then reduced by the action of (c) an organometallic reducing compound to produce the highly active hydrogenation catalyst.

Considering in more detail ingredient (a) of the soluble catalyst precursor, that is, the organic chelate compound of a transition metal, this is usuallly a compound of nickel, cobalt or iron with a chelating agent such as a beta-diketone or a beta-ketoester. Examples of the chelating agents include acetylacetone, 1,3-hexanedione, 3,5-nonadione, methylacetoacetate, ethylacetoacetate and the like.

To arrive at the soluble precursor, the described organic chelate compound of a transition metal (a) is, as indicated, contacted with (b) a phenolic substance, thus producing a soluble organometallic complex. For this purpose phenol itself is suitable, or there may be used a substituted phenol such as a monoalkylphenol having an alkyl group of for example 1 to 10 carbon atoms, typically in the 2- or 4- position, or a dialkylphenol usually having the alkyl groups (having for example 1 to 10 carbon atoms in each group) in the 2,4- or 2,6- positions. Examples of such phenols include 2-butylphenol, 2-t-butylphenol, 2-octylphenol, 2-t-octylphenol, 2-nonylphenol, 4-butylphenol, 4-t-butylphenol, 4-octylphenol, 4-t-octylphenol, 4-nonylphenol, 2-methyl-4-ethylphenol, 2-ethyl-4-butylphenol, 2,4-dipropylphenol, 2,4-di-t-butylphenol, 2-butyl-4-t-octylphenol, 2,4-dinonylphenol, 2-methyl-6-ethylphenol, 2-ethyl-6-t-butylphenol, 2,6-dipropylphenol, 2,6-di-t-butylphenol, 2-methyl-6-t-octylphenol, 2-butyl-6-t-octylphenol, 2,6-dinonylphenol and the like.

The organometallic soluble catalyst precursor is conveniently made by bringing (a) the transition metal chelate and (b) the phenolic substance together in the presence of an organic solvent medium. For this purpose inert solvents in general are suitable, or, when the material to be hydrogenated is a liquid under the conditions prevailing, such material may be used as the solvent. Frequently the inert solvent is a hydrocarbon solvent. Frequently the inert solvent is a hydrocarbon solvent, whether saturated (aliphatic, or cycloaliphatic) or aromatic, or combined forms such as hydroaromatic, or mixtures of such solvents may be used. Examples include hexane, heptane, octane, benzene, toluene, xylene, cyclohexane, methylcyclohexane, decalin, tetralin, etc. The solvent may contain, dissolved therein, a material to be hydrogenated. The conditions under which the soluble organometallic complex is formed by interaction of the transition metal chelate and the phenolic material are not critical. Usually the mixing is carried out, with stirring, at somewhat elevated temperature (e.g., 60°–90°C) and the reaction is frequently sufficiently completed within a period of a few minutes although longer reaction times (e.g., 1 or 2 hours or more) may also be used. The organometallic catalyst precursor will remain soluble when the solution is cooled to room temperature. If isolated from the solution it is usually a glassy solid whose color depends upon the transition metal used, but isolation is not necessary. The relative proportions of transition metal chelate to phenolic substance are not critical and may vary. Usually at least about ½ mole of transition metal chelate is used per mole of phenolic material. Larger quantities may be used, such as for example up to about 2 moles of transition metal chelate per mole of phenolic material. Frequently it is preferred to use approximately equimolar quantities of transition metal chelate and phenolic substance.

Having thus provided the soluble organometallic complex catalyst precursor, the next stage in the method of making the catalyst involves, as indicated, subjecting the precursor to the action of an organometallic reducing agent (c) in the solvent medium. Particularly suitable organometallic reducing compounds are those having the formula $MR_n$, where M is a metal such as lithium, magnesium or aluminum, R is a hydrocarbon radical, and n is the valence of the metal. The hydrocarbon radical R may be saturated (acyclic or cyclic) or aromatic. Especially useful are those compounds in which R has for example up to 12 carbon atoms, as in saturated acyclic hydrocarbon radicals having 1 to 12 carbon atoms, saturated cyclic hydrocarbon radicals having 5 to 12 carbon atoms, and aromatic hydrocarbon radicals having 6 to 12 carbon atoms. Examples of such radicals include alkyl, aryl, alkaryl, aralkyl and cycloaliphatic groups exemplified by methyl, ethyl, n-propyl, i-propyl, n-butyl, i-butyl, sec-butyl, t-butyl, pentyl, hexyl, heptyl, octyl, nonyl, dodecyl, phenyl, benzyl, tolyl, cyclopentyl, cyclohexyl, and naphthyl radicals. Thus, examples of the organometallic reducing compounds include ethyllithium, n-propyllithium, n-butyllithium, i-butyllithium, sec-butyllithium, t-butyllithium, n-pentyllithium phenyllithium, diethylmagnesium, di-n-propylmagnesium, di-n-butylmagnesium, diphenylmagnesium, triethylaluminum, tri-n-propylaluminum, triisopropylaluminum, tri-n-butylaluminum, triisobutylaluminum, triamylaluminum, trihexylaluminum, trioctylaluminum, trididecylaluminum, diethylisobutylaluminum, diethyloctylaluminum, tricyclohexylaluminum, triphenylaluminum and their mixtures.

When the solution of the organometallic complex catalyst precursor and the described organometallic reducing compound (c) are brought together to form the catalyst of the invention, formation of the catalyst is immediate, even at room temperature, and is indicated by the development of a brown or black color. The proportions of organometallic complex to reducing compound (c) suitable for forming the catalyst may vary. Ordinarily at least about 1 mole of the reducing compound (c) is employed for each mole of components (a) plus (b). It is frequently preferred to use a molar excess of organic reducing compound (c), for example, the molar amount of compound (c) is advantageously about 3 times the molar sum of components (a) and (b). A preferred range of (c) in 2 to 5 times the sum of (a) and (b). While there is no upper limit to the amount of reducing substance that may be employed, and larger amounts can be used, there is no proportionate added advantage in using such larger amounts and for reasons of economy larger amounts will not ordinarily be used. Slow addition of the reducing compound is preferred since this has been found to assure the formation of a highly active fine dispersion of the pre-reduced metal hydrogenation catalyst. In practice a convenient procedure is to add the reducing agent slowly or in portions with good stirring over a short period of time.

To carry out the hydrogenation process of the invention the substance to be hydrogenated is contacted with hydrogen in the presence of the described catalyst composition. Any organic substance having a non-aromatic hydrogenatable carbon-to-carbon unsaturated bond is operable in the invention, including substances with one or more ethylenic (olefinic) or acetylenic multiple bonds. The hydrogenatable substances include not only low molecular weight or monomeric substances, but also high molecular weight or polymeric substances. Examples of monomeric non-polymeric materials that may be hydrogenated include unsaturated hydrocarbon monomers, particularly monoolefins having 2 to 12 carbon atoms such as ethylene, propylene, cis-2-butene, trans-2-butene, 2-methylbutene-1, 2-methylbutene-2, 1-pentene, 2-pentene, 1-hexene, 1-heptene, 1-octene, isooctene, styrene, vinyl toluene and the like.

Examples of polymers which may be hydrogenated include such unsaturated hydrocarbon polymers as the diene polymers, whether homopolymers or copolymers. Of particular importance are the homopolymers and copolymers of conjugated dienes, including copolymers of connjugated dienes with each other and with copolymerizable ethylenically unsaturated monomers such as the vinyl-substituted aromatic hydrocarbons. Examples of such polymers include polybutadiene, polyisoprene, butadiene-styrene copolymers, butadiene-alpha-methylstyrene copolymers, butadieneisoprene copolymers, polybutadiene grafted with a minor amount of styrene, and others. These polymers may be prepared by bulk polymerization, solution polymerization, or emulsion polymerization by the use of a radical type initiator, an ionic type initiator, or a Ziegler type initiator. The hydrogenated polymers obtained from these polymers are useful for manufacturing rubber articles. In addition to polymers based on conjugated dienes, polymers based on non-conjugated dienes may be used, notably the EPDM class of polymers. These are ordinarily sulfur-curable, chain-saturated terpolymers of a major proportion of ethylene and propylene and a minor amount (sufficient to confer sulfur-vulcanizability) of a non-conjugated diene such as an acyclic diolefin (e.g., 1,4-hexadiene) or a polycyclic diene (e.g., dicyclopentadiene, cyclooctadiene, alkylidene norbornenes or mixtures of such dienes, such as dicyclopentadiene in admixture with ethylidene norbornene, methyl tetrahydroindene, etc.). Usually the preferred EPDM rubbery copolymers contain ethylene and propylene in a weight ratio of from 20:80 to 75:25 and the diene content ranges up to about 20% by weight of the polymer (usually up to 10%). U.S. Pat. No. 2,933,480, Gresham et al., Apr. 19, 1960; U.S. Pat. No. 3,000,866 Tarney, Sept. 19, 1961; U.S. Pat. No. 3,063,973, Gladding et al., Nov. 13, 1962; U.S. Pat. No. 3,043,620, Gladding et al., June 11, 1963; and U.S. Pat. No. 3,211,709, Adamek et al., Oct. 12, 1965, teach examples of suitable alpha-olefin copolymers to which this invention is applicable.

As indicated previously, the substance to be hydrogenated may be present in the solution in which the catalyst is prepared, and, in fact, when the substance to be hydrogenated is a liquid it may itself serve as the solvent. Otherwise, any inert hydrocarbon solvent as previously described may serve as the solvent medium for the hydrogenation. The substance to be hydrogenated is preferably present when the active catalyst is formed by the action of the reducing agent on the soluble precursor. Less preferably the substance to be hydrogenated is added to the solution subsequent to preparation of the catalyst. There are no restrictions on the concentration of the hydrogenatable substance in the solution and such concentration can range all the way from less than 1% by weight up to the limit of solubility, if any, of the hydrogenatable substance in the solvent, all the way to 100% in the case where the hydrogenatable substance itself serves as the solvent. Ordinarily the concentration of the solution of a polymer to be hydrogenated may be varied as desired, for example, from less than 1% to greater than 30%, preferably from about 1 to 20%. The concentration of the solution of a non-polymeric unsaturated compound to be hydrogenated similarly may ordinarily be varied as desired, for example from 1% or less, and higher for those which are solid at room temperature, to about 100% for those which are liquid at the hydrogenation temperature.

The hydrogenation process of the invention is typically carried out by bubbling hydrogen into the solution containing a catalytic amount of the catalyst and the material to be hydrogenated, usually with stirring or shaking depending upon the type of reaction vessel being used. Usually the relative amounts of catalyst and hydrogenatable substance present are such that the mixture contains from about 150 moles or more to 1 moles or less of carbon-to-carbon unsaturation (olefinic double bonds) per mole of transition metal, the preferred amount being about 1 to 20 moles of carbon-to-carbon unsaturation per mole of transition metal. The hydrogenation proceeds under mild hydrogenation conditions, including ambient temperature and pressure. If desired elevated pressure (e.g. 10 atmospheres or higher) may be used for greater efficiency. Typically a convenient pressure range is from about 14 to 50 psig. It is not necessary to exercise special control over the temperature of the reaction mixture, but if desired the mixture may be cooled (e.g., to 10°C or less) or heated (e.g. to 100°C or more). Frequently the hydrogenation is carried out at a temperature of from 25° to 75°C. The hydrogenation is rapid and sometimes requires only a few minutes (e.g. 5 minutes) although longer reaction times (e.g. about 1 to 10 hours or more) may be used if desired.

After the hydrogenation has been completed to the desired extent, the catalyst may be deactivated by adding a polar solvent such as acetone or alcohol, preferably containing an excess of mineral acid such as aqueous hydrochloric acid. The hydrogenated substance may be recovered in any suitable conventional manner. In the case of a hydrogenated polymer, addition of the polar solvent ordinarily causes precipitation of the polymer. To prevent any oxidation of the polymer during the recovery operations, a small amount (e.g. 0.25 to 0.75%) of a conventional rubber antioxidant may be added. The extent of hydrogenation of the product may be determined by any of several methods including refractive index, titration, or gas phase chromatography.

In accordance with a preferred practice of the invention the active catalyst-formation step, that is, the step involving reduction of the dissolved soluble organometallic complex catalyst precursor by action of the organometallic reducing agent (c), is carried out in the presence of hydrogen, and more preferably in the presence of both hydrogen and the substance to be hydrogenated. Such in-situ formation of the active catalyst in the hydrogenation mixture insures the formation of a catalyst which is highly effective.

The invention is remarkable for the efficiency with which otherwise difficult to hydrogenate materials can be hydrogenated. Polyisoprene for example has previously been difficult to hydrogenate. In certain prior hydrogenation processes polyisoprene tends to degrade but such is not the case in the present process. By use of the present process polybutadiene can be partially hydrogenated to provide an improved material having less cold flow and improved gum tensile strength. The present catalyst is extremely active. The catalyst is not sensitive to small traces of impurities such as water and does not require the vigorous control of reagent ratios required in certain prior art systems. The catalyst may contain considerable quantities of impurities and commercial grades of solvents may be used while still maintaining high activity. The present catalyst is superior to typical prior catalysts in the degree and rapidity of hydrogenation which is possible.

The following examples will serve to illustrate the practice of the invention in more detail.

EXAMPLE 1

This example illustrates the preparation of the soluble metal complex using nickel acetyl acetonate as the source of the transition metal and the hydrogenation ability of the catalyst of this invention formed from the soluble nickel complex.

A mixture of 0.24 mole (61.4g) of nickel acetylacetonate, 0.24 mole (52.8g) of commercial grade p-nonylphenol and 300 ml. of n-heptane is stirred and heated at 80°–90°C. for 1 hour. The resultant solution of the heptane soluble nickel complex is cooled to room temperature and stored in a capped bottle.

400 ml. of a 2% by weight solution of polyisoprene (equivalent to 0.12 moles of olefinic unsaturation calculated as moles of monomer or isoprene) in n-hexane is placed in a dry 600 ml. narrow neck beverage bottle. The polyisoprene is a material sold under the trademark "Natsyn 400" by Goodyear Tire & Rubber Co., having a Mooney viscosity of 85 (ML-4 at 212°F). To this polyisoprene solution is added 20 ml of the above metal complex solution (equivalent to 16 mmoles of nickel) and the mixture is flushed with hydrogen. To the resultant mixture is added 50 mmole of n-butyllithium as a 1.6 molar n-hexane solution during a period of 10 minutes with stirring. The slow addition of the reducing compound (n-butyllithium) results in a highly active nickel hydrogenation catalyst. After the addition of the n-butyllithium, the resultant mixture is contacted with hydrogen under a pressure of 14 psig at room temperature (25°C) by bubbling hydrogen into the mixture for a period of 60 minutes. 2,2'-Methylenebis(4-methyl-6-t-butylphenol) (one part/100 of polymer) and polyetherdiamine (reaction product of polypropylene glycol and propylene imine, molecular weight 2000; three parts/100 of polymer) are then added to protect the partially hydrogenated polymer from oxidation and for efficient catalyst removal. The resultant mixture is then washed twice with 500 ml. of 50% aqueous hydrochloric acid and the polyisoprene is flocculated by the addition of an excess of isopropyl alcohol containing 2,2'-methylene bis(4-methyl-6-t-butylphenol). The wet polymer crumb is dried overnight at 35°C in a vacuum oven. Analysis of the polyisoprene using refractive index shows the polyisoprene to be 45% hydrogenated. The intrinsic viscosity at 135°C. in tetralin of the hydrogenated polymer is 1.07 compared 1.02 for the original polymer. The experiment is summarized as Run 1 in Table I.

The experiment demonstrates the outstanding hydrogenation activity of the catalyst of this invention at room temperature and low hydrogen pressure, without any degradation of the polymer.

The experiment is repeated, except that the p-nonylphenol is omitted. Analysis of the resultant polymer shows only 8% hydrogenation. The experiment is summarized as Run 2 in Table I.

For purposes of comparison, a third run is made, identified as Run 3 in Table I, according to the procedure of Run 1 but substituting nickel naphthenate for the soluble nickel complex. Run 3 is outside the invention and employs 400 ml. of a 1% by weight n-hexane solution of polyisoprene using commercial grade nickel naphthenate as the source of the soluble transition metal. 15 mmoles of nickel naphthenate is reduced with 50 mmoles of n-butyllithium giving, as indicated in Table I, a [RA]/[Me] ratio of 3.3 and a [C=C]/[Me] ratio of 3.9. The percent hydrogenation of the polymer as measured by refractive index is 8 percent. The intrinsic viscosity at 30°C in toluene before hydrogenation is 4.16 and after hydrogenation it is 2.53 indicating that a significant amount of polymer degradation has occurred.

TABLE I

| | Example 1 - Hydrogenation of Polyisoprene | | | | | | | |
|---|---|---|---|---|---|---|---|---|
| Run | Transition Metal [Me] | Phenol | Reducing Compound [RA] | Molar Ratio [RA]/[Me] | Molar Ratio [C=C]/[Me] | Percent Hydrogenation | Polymer Intrinsic Viscosity Before | After |
| 1 | nickel acetylacetonate | p-nonylphenol | n-butyllithium | 3 | 7.3 | 45 | 1.07 (tetralin 135°C) | 1.02 (tetralin 135°C) |
| 2 | nickel acetylacetonate | — | n-butyllithium | 3 | 7.3 | 8 | — | — |
| 3 | nickel naphthenate | — | n-butyllithium | 3.3 | 3.9 | 8 | 4.16 (toluene 30°C) | 2.53 (toluene 30°C) |

EXAMPLE 2

The hydrogenation activity of the catalyst of this invention can be significantly increased by utilizing hydrogen pressures above one atmosphere as demonstrated by the following example. 400 ml. of a 2.5% by weight n-hexane solution of polyisoprene (commercial material known as "Isoprene 305", Shell Chemical Co.; 70–90 Mooney viscosity [ML-4 at 212°F]) was placed in a 500 ml capacity Paar hydrogenation apparatus. A solution of 16 mmoles of soluble nickel complex prepared as in Run 1 of Example 1 was added to the polymer solution. After flushing with hydrogen, 50 mmoles of n-butyllithium was added over a period of 10 minutes and the solution was contacted, while shaking, with hydrogen at 50 psig pressure and room temperature for 60 minutes. The recovered polymer indicated 78% hydrogenation with an intrinsic viscosity of 1.36 as measured in tetralin at 135°C. The intrinsic viscosity of the original polymer was 0.81, indicating that hydrogenation resulted in an increase in the molecular weight of the polymer. The experiment is summarized as Run 4 in Table II.

In Run 5, the Run 4 experiment is repeated except that aged catalyst is used, that is, all the catalyst ingredients are combined (in the absence of polyisoprene and hydrogen) and stored for 4 hours in a stoppered bottle at room temperature under a nitrogen atmosphere before use, with the results given in Table II. Run 5 demonstrates that aging of the catalyst at room temperature for a period up to 4 hours does not have any significant deleterious effect on the hydrogenation capability.

a hydrogen pressure of 30 psig was applied. The degree of hydrogenation was followed by the refractive index of the polymer as shown in Table III.

TABLE III

| Example 3 - Hydrogenation of Polyisoprene (Run 6) | |
|---|---|
| Reaction Time minutes at 75°C. | Percent Hydrogenation |
| 30 | 57 |
| 60 | 71 |
| 120 | 77 |

EXAMPLE 4

The following runs (Runs 7, 8, 9 and 10, Table IV) were made to demonstrate the effect of the catalyst level in terms of mmoles of nickel on the hydrogenation of a polymer. The catalyst of this invention was compared with a prior art catalyst made from a soluble nickel salt (nickel naphthenate). The experimental procedure and reaction conditions were the same as in Run 1 of Example 1. The results are summarized in Table IV.

TABLE IV

| | Example 4 - Hydrogenation of Polyisoprene | | | | | | | |
|---|---|---|---|---|---|---|---|---|
| Run | Transition Metal [Me] | Phenol | Reducing Compound [RA] | Molar Ratio [RA]/[Me] | Molar Ratio [C=C]/[Me] | Mmoles of Ni | Reaction Time at 25°C Mins. | Hydrogen pressure psig | Percent Hydrogenation |
| 7 | nickel acetylacetonate | p-nonyl phenol | n-butyllithium | 31 | 37 | 1.56 | 60 | 14 | 6 |
| 8 | " | " | " | 3.1 | 3.7 | 15.6 | 60 | 14 | 57 |
| 9 | " | " | " | 0.8 | 0.93 | 62.3 | 60 | 14 | 51 |
| 10 | nickel naphthenate | — | " | 0.8 | 0.93 | 62.3 | 60 | 14 | 25 |

EXAMPLE 5

The catalyst of this invention exhibits activity for the hydrogenation of low-unsaturation, sulfur-vulcanizable EPDM-type elastomers. Run 1 of Example 1 was repeated using 400 ml of a 2% by weight n-hexane solution of a commercial EPDM elastomer which was a solution polymerized terpolymer of ethylene/propylene/5-ethylidene-2-norbornene (ratio of ethylene to propylene 60:40, by weight), having an iodine number of 28.8, and an intrinsic viscosity in tetralin at 135°C of 1.73. The iodine number of the hydrogenated polymer was 11.6 indicating that the percent hydrogenation was 60.

TABLE II

| | Example 2 - Hydrogenation of Polyisoprene | | | | | | | | |
|---|---|---|---|---|---|---|---|---|---|
| Run | Transition Metal [Me] | Penol | Reducing Compound [RA] | Aging of Catalyst hrs at R.T. | Molar Ratio [RA]/[Me] | Molar Ratio [C=C]/[Me] | Hydrogen Pressure psig | Percent Hydrogenation | Polymer Intrinsic Viscosity Before | After |
| 4 | nickel acetylacetonate | p-nonyl phenol | n-butyllithium | 0 | 3 | 9.8 | 50 | 78 | 0.81 | 1.36 |
| 5 | nickel acetylacetonate | p-nonyl phenol | n-butyllithium | 4 | 3 | 9.8 | 50 | 75 | 0.81 | 0.97 |

EXAMPLE 3

The extent of polymer hydrogenation can be increased with increasing time as demonstrated by the following run (Run 6, Table III):

300 ml. of a 1% by weight n-hexane solution of polyisoprene (Natsyn 400) was introduced into a 1-gallon capacity glass pressure reactor equipped with an air driven stirrer. 50 mmoles of the soluble nickel complex of Run 1 of Example 1 was added to the polymer solution and the mixture flushed with hydrogen. Over a 10 minute period, 250 mmoles of n-butyllithium was added, after which the reaction was heated to 75°C and kept at this temperature for 2 hours during which time

EXAMPLE 6

A portion of the partially hydrogenated polymer of Run 1 of Example 1 was hydrogenated twice more using the procedure of Example 1. The resulting polymer was 100% hydrogenated with an intrinsic viscosity of 2.29 compared with 1.02 for the original polymer (in tetralin at 125°C).

EXAMPLE 7

The following example demonstrates the utility of the catalysts of the present invention in the hydrogenation of low molecular weight alpha-olefin monomers.

Following the procedure of Example 1, soluble metal complexes were made from ferric acetylacetonate and nickel acetylacetonate as indicated in Runs 11 and 13 in Table V. These metal complexes were then used to hydrogenate 10 ml (0.063 moles) of 1-octene dissolved in 200 ml of cyclohexane in a 600 ml narrow neck beverage bottle. In each case the metal complex was added to the solution of the alpha-olefin, flushed with hydrogen, and an excess amount of n-butyllithium added over a period of 10 minutes. The reaction mixture was then contacted with hydrogen at 14 psig and room temperature for 60 minutes. Companion runs without any phenol (Runs 12 and 14, Table V) in the catalyst mixture were run to demonstrate the effect of the unique solubilization action of the phenol. In all cases the reducing agent to transition metal mole ratio was between 6:1 and 10:1. The results are given in Table V.

TABLE V

Example 7 - Hydrogenation of 1-Octene

| Run | Transition Metal [Me] | Phenol | Reducing Compound [RA] | Mmoles of Metal, Me | Percent Hydrogenation |
|---|---|---|---|---|---|
| 11 | ferric acetylacetonate | p-nonyl phenol | n-butyllithium | 0.54 | 56 |
| 12 | '' | — | '' | 0.70 | 12 |
| 13 | nickel acetylacetonate | p-nonyl phenol | '' | 0.79 | 35 |
| 14 | '' | — | '' | 0.70 | 25 |

Having thus described our invention, what we claim and desire to protect by Letters Patent is:

1. A method of making a hydrogenation catalyst comprising in combination the steps of:
   A. forming a hydrocarbon-soluble organometallic complex by contacting, in a hydrocarbon solvent medium,
      a. an organic chelate compound of a transition metal selected from the group consisting of nickel, cobalt and iron with a chelating agent selected from the group consisting of beta-diketone and beta-ketoester, with
      b. a phenolic substance selected from the group consisting of phenol, 2-alkylphenol, 4-alkylphenol, 2,4-dialkylphenol and 2,6-dialkylphenol wherein each alkyl group contains 1 to 10 carbon atoms,
   the amount of (a) being from ½ to 2 moles, per mole of (b); and thereafter
   B. mixing the resulting solution of hydrocarbon-soluble organometallic complex provided in step (A) with
      c. an organometallic reducing agent of the formula $MR_n$ where M is a metal selected from the group consisting of lithium, magnesium and aluminum, R is a hydrocarbon radical selected from the group consisting of saturated acyclic hydrocarbon radical having 5 to 12 carbon atoms and aromatic hydrocarbon radical having 6 to 12 carbon atoms, and n is the valence of the metal M,
   the amount of (c) being from 1 to 5 moles per combined moles of said organic chelate compound (a) plus said phenolic substance (b), whereby the said hydrogenation catalyst is produced in highly active form.

2. A method as in claim 1 in which the said transition metal is nickel.

3. A method as in claim 1 in which the said transition metal is iron.

4. A method as in claim 1 in which the said chelating agent is a beta-ketoester.

5. A method as in claim 4 in which the said chelating agent is acetylacetone.

6. A method as in claim 1 in which the said phenolic substance is a 4-alkylphenol.

7. A method as in claim 6 in which the 4-alkylphenol is 4-nonylphenol.

8. A method as in claim 1 in which the said metal M in said organometallic reducing agent is lithium.

9. A method as in claim 1 in which the said hydrocarbon radical R in said organometallic reducing agent is a saturated acyclic hydrocarbon radical having 1 to 12 carbon atoms.

10. A method as in claim 9 in which the said organometallic reducing agent is n-butyllithium.

11. A method as in claim 1 in which equimolar amounts of (a) and (b) are employed, and the amount of (c) is from 2 to 5 moles per combined moles of (a) plus (b).

12. A method as in claim 1 in which the said step (B) is carried out in the presence of a substance to be hydrogenated which is a hydrocarbon having an olefinic double bond, and hydrogen.

13. A hydrogenation catalyst produced by the method of claim 1.

14. A hydrogenation catalyst as in claim 13 in which the said transition metal is nickel, the said chelating agent is a beta-ketoester, the said phenolic substance is a 4-alkylphenol, the said metal M in $MR_n$ is lithium and the said hydrocarbon radical R is a saturated acyclic hydrocarbon radical having 1 to 12 carbon atoms.

15. A hydrogenation catalyst as in claim 13 in which (a) is nickel acetylacetonate, (b) is 4-nonylphenol, and (c) is n-butyllithium.

* * * * *